(12) United States Patent
Zhang et al.

(10) Patent No.: US 12,234,520 B1
(45) Date of Patent: Feb. 25, 2025

(54) MOLECULAR MARKER SIGNIFICANTLY ASSOCIATED WITH VITAMIN E CONTENT IN SOYBEANS, KOMPETITIVE ALLELE SPECIFIC POLYMERASE CHAIN REACTION PRIMERS COMBINATION AND APPLICATION THEREOF

(71) Applicant: Jiangsu Academy of Agricultural Sciences, Nanjing (CN)

(72) Inventors: Hongmei Zhang, Nanjing (CN); Wei Zhang, Nanjing (CN); Huatao Chen, Nanjing (CN); Qiong Wang, Nanjing (CN); Xiaoqing Liu, Nanjing (CN); Qianru Jia, Nanjing (CN)

(73) Assignee: Jiangsu Academy of Agricultural Sciences, Nanjing (CN)

( * ) Notice: Subject to any disclaimer, the term of this patent is extended or adjusted under 35 U.S.C. 154(b) by 0 days.

(21) Appl. No.: 18/802,544

(22) Filed: Aug. 13, 2024

(30) Foreign Application Priority Data

Dec. 13, 2023 (CN) .......................... 202311719318.0

(51) Int. Cl.
*C12Q 1/68* (2018.01)
*C12Q 1/6895* (2018.01)

(52) U.S. Cl.
CPC ....... *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2017/0027122 A1 | 2/2017 | Hanson et al. |
| 2019/0352658 A1 | 11/2019 | Herman |
| 2022/0154202 A1 | 5/2022 | Stacey et al. |

FOREIGN PATENT DOCUMENTS

| | | |
|---|---|---|
| CN | 113637786 A | 11/2021 |
| CN | 113801953 A | 12/2021 |
| CN | 116287423 A | 6/2023 |
| CN | 116926229 A | 10/2023 |
| WO | 2015004328 A2 | 1/2015 |

OTHER PUBLICATIONS

Glycine max cultivar Williams 82 chromosome 12, GenBank CP126437.1. Aug. 23, 2023, Showing 403 bp region from base 987017 to 987419. (Year: 2023).*
Wang Yan et al., "The Advance of Molecular Markers in Soybean," Soybean Science, Feb. 2015, pp. 1,066-1,074, vol. 34, No. 1. Related claims: 1-10.
First Office action for China Application No. 202311719318.0, mailed Mar. 27, 2024.
Notification to Grant Patent for China Application No. 202311719318.0, mailed Apr. 21, 2024.
First Search Report for China Application No. 202311719318.0, dated Mar. 25, 2024.
Supplementary Search Report for China Application No. 202311719318.0, dated Apr. 11, 2024.

* cited by examiner

*Primary Examiner* — Juliet C Switzer
(74) *Attorney, Agent, or Firm* — Piloff Passino & Cosenza LLP; Rachel K. Piloff; Sean A. Passino

(57) ABSTRACT

A molecular marker significantly associated with vitamin E content in soybeans, a Kompetitive Allele-Specific polymerase chain reaction (KASP) primers combination and an application thereof are provided in the present disclosure, belonging to the field of molecular genetics and breeding. A nucleotide sequence of the molecular marker is shown in SEQ ID NO. 1, and there is an A/T mutation at the 21st base. The KASP primer set for detecting the molecular marker includes an upstream primer F1 with a nucleotide sequence as shown in SEQ ID NO. 2, an upstream primer F2 with a nucleotide sequence as shown in SEQ ID NO. 3 and a downstream primer r with a nucleotide sequence as shown in SEQ ID NO. 4. The KASP primers combination developed by the present disclosure accurately distinguish soybeans with high and low vitamin E content.

4 Claims, 7 Drawing Sheets

Specification includes a Sequence Listing.

MOLECULAR MARKER SIGNIFICANTLY ASSOCIATED WITH VITAMIN E CONTENT IN SOYBEANS, KOMPETITIVE ALLELE SPECIFIC POLYMERASE CHAIN REACTION PRIMERS COMBINATION AND APPLICATION THEREOF

CROSS-REFERENCE TO RELATED APPLICATIONS

This application claims priority to Chinese Patent Application No. 202311719318.0, filed on Dec. 13, 2023, the contents of which are hereby incorporated by reference.

INCORPORATION BY REFERENCE STATEMENT

This statement, made under Rules 77 (b) (5) (ii) and any other applicable rule incorporates into the present specification of an XML file for a "Sequence Listing XML" (see Rule 831 (a)), submitted via the USPTO patent electronic filing system or on one or more read-only optical discs (see Rule 1.52 (e) (8)), identifying the names of each file, the date of creation of each file, and the size of each file in bytes as follows:
  File name: PPH-US 2024-7162 Sequence
  Creation date: Oct. 19, 2024
  Byte size: 5,213

TECHNICAL FIELD

The present disclosure relates to the field of molecular genetics and breeding, and in particular to a molecular marker significantly associated with vitamin E content in soybeans, a Kompetitive Allele Specific polymerase chain reaction (KASP) primers combination and an application thereof.

BACKGROUND

Vitamin E (VE), also known as tocopherol, consists of eight homologs of alpha ($\alpha$), beta ($\beta$), gamma ($\gamma$) and delta ($\delta$) tocopherols and their corresponding trienyl tocopherols. At room temperature, the bioactivities are =$\alpha$>$\beta$>$\gamma$>$\delta$, with $\alpha$-tocopherol having the strongest physiological activity and $\gamma$-tocopherol having the strongest antioxidant capacity, while $\beta$-tocopherol is very low in content and is generally ignored in studies of VE content. Vitamin E has been shown to be effective in improving immunity, anti-aging, anti-infertility, anti-cancer and prevention of cardiovascular diseases. Natural sources of vitamin E are mainly economic oil crops, including soybeans, sunflower seeds and rapeseed. Among them, the vitamin E content of soybeans is at the top of the list, ranging from 0.09% to 0.28%. As a natural antioxidant in soybean oil, Vitamin E serves to protect the flavor and prolong the storage life of fats and oils that affect seed longevity, and to ensure seed viability after prolonged storage. Therefore, it is of great production importance to study rapid and effective molecular breeding techniques concerning soybean vitamin E traits for molecularly assisted genetic improvement of soybean vitamin E quality traits.

Traditional soybean breeding for vitamin E involves single-plant selection based on the content of vitamin E fractions in the breeding progeny, which is not only time-consuming and labor-intensive but also susceptible to environmental interference with low accuracy. Assisted selection by developing specific molecular markers utilizing base differences in the target genes is an optimal method to improve the selection efficiency of soybeans with high vitamin E content. With the advantages of early selection, independence from environmental influences as well as accuracy, speed and efficiency, molecular markers have become an accurate and efficient tool in crop breeding. Among them, Kompetitive allele specific PCR (KASP) is a homogenous, fluorescence-based genotyping variant of polymerase chain reaction. It is based on allele-specific oligo extension and fluorescence resonance energy transfer for signal generation. There are two allele-specific forward primers, and a common reverse primer for the KASP markers based on the allele SNP, and each forward primer has specific sequence that binds to different fluorescent markers. Forward primers with sequences that bind to different fluorescence and common reverse primers amplify DNA from samples by PCR, and the allelic variation may then be reflected by different fluorescence signals.

Studies have shown that the vitamin E content of soybean is a complex quantitative trait that is regulated by multiple genes and is susceptible to environmental influences. Currently, several quantitative trait loci (QTL) controlling vitamin E content in soybean have been reported in existing studies. Single nucleotide polymorphism (SNP) mainly refers to DNA sequence polymorphism caused by variation in a single nucleotide at the genomic level. Genome wide association study (GWAS), as an effective gene targeting tool, enables rapid and accurate mining of SNP significantly associated with soybean vitamin E. Based on the identified SNP significantly associated with soybean vitamin E, the KASP markers closely associated with the content of soybean vitamin E are developed and used for the selection of soybean vitamin E at the early stage of the breeding process (low generation), which is a significant contribution to reducing the workload of the breeding process and accelerating the progress of the breeding process, and at the same time, the economic benefits are obvious. Therefore, it is particularly important to develop KASP molecular markers for breeding assistance based on mining SNP significantly associated with soybean vitamin E to realize molecular-assisted selection of target traits at early stage in order to improve the breeding efficiency.

SUMMARY

The objective of the present disclosure is to provide a molecular marker significantly associated with vitamin E content in soybeans, a Kompetitive Allele-Specific polymerase chain reaction (KASP) primers combination and an application thereof, so as to solve the problems existing in the prior art. The KASP primers combination developed by the present disclosure is capable of directly distinguishing and detecting specifically the A or T bases of SNP mutation sites, which has good application value and enables pre-selection and molecular-assisted breeding of vitamin E content traits in soybeans, and is of great theoretical and practical guidance for accelerating the process of genetic improvement in breeding for vitamin E content and improving the efficiency of breeding selection.

In order to achieve the above objectives, the present disclosure provides the following scheme.

The present disclosure provides a molecular marker significantly associated with vitamin E content in soybeans, where the molecular marker has a nucleotide sequence as shown in SEQ ID NO. 1, with an A/T mutation at a 21st base.

The present disclosure also provides a KASP primer set for detecting the molecular marker, including an upstream primer F1 with a nucleotide sequence as shown in SEQ ID NO. 2, an upstream primer F2 with a nucleotide sequence as shown in SEQ ID NO. 3 and a downstream primer R with a nucleotide sequence as shown in SEQ ID NO. 4.

The present disclosure also provides a detection kit of the molecular marker, including the KASP primer set.

The present disclosure also provides an application of the KASP primer set or the detection kit in identifying vitamin E content in soybeans.

The present disclosure also provides a method for identifying vitamin E content in soybeans, including the following steps:
  using a genomic DNA of a soybean sample to be detected as a template, performing fluorescence quantitative PCR amplification on the template by using the KASP primer set or the detection kit, reading a fluorescence signal after PCR amplification, analyzing and converting the fluorescence signal, identifying a genotype, and determining soybean vitamin E content to be high (≥160.0 μg/g) or low (≤30.0 μg/g) based on the genotype;
  if the genotype is identified as TT, the soybean sample to be detected is determined to have a high vitamin E content; if the genotype identified is AA, the soybean sample to be detected is judged to have a low vitamin E content.

Optionally, a procedure of the fluorescence quantitative PCR amplification includes: activation at 94 degrees Celsius (° C.) for 15 minutes (min); denaturation at 94° C. for 20 seconds (sec), annealing at 61-55° C. for 60 sec, decreasing 0.6° C. per cycle for 10 cycles; denaturation at 94° C. for 20 sec, annealing at 55° C. for 60 sec for 26 cycles.

Optionally, a system of the fluorescence quantitative PCR amplification includes: 25 nanogram per microliter (ng/μL) DNA template 2 μL, 2×KASP Master mix 5 μL, KASP mixed primer 0.14 μL, where a volume ratio of the upstream primer F1, upstream primer F2 and downstream primer R is 2:2:5, and water 2.86 μL.

The present disclosure also provides an application of the KASP primer set or the detection kit in screening soybean varieties or strains with high vitamin E content.

The present disclosure also provides an application of the KASP primer set or the detection kit in molecular marker-assisted breeding of soybean vitamin E content traits.

Optionally, high and low vitamin E content of different soybean isolated generations are identified using the KASP primer set or the detection kit, and single plants or strains with high vitamin E content are selected for cultivation.

The present disclosure achieves the following technical effects.

The SNP significantly associated with soybean vitamin E provided by the present disclosure is obtained from 264 representative soybean germplasm resources (including 52 local species and 212 cultivars) screened by genome wide association study (GWAS) based on the phenotypic data of soybean vitamin E components, and the phenotypic variance explained rate of this SNP locus reaches 9.6%, which is located in a position of 980,498 bp of chromosome 12, soybean genome v2.0, providing technical support for molecular marker-assisted breeding of soybean vitamin E content traits.

The KASP primers combination developed by the present disclosure is capable of directly distinguishing and detecting specifically the A or T bases of the SNP mutation site, and when the high or low content of soybean vitamin E is identified using this KASP primers combination, it is capable of clearly separating the two genotypes, in which the triangles close to the Y-axis are the T allele-carrying soybean varieties, and the content of soybean vitamin E in this genotype is relatively high; the black dots near the X-axis represent soybean varieties carrying allele AA, which has a relatively low content of vitamin E in soybeans. The KASP primers combination developed by the present disclosure has good application value and may realize pre-selection and molecular-assisted breeding for soybean vitamin E content traits, which is of great theoretical and practical guidance significance for accelerating the process of genetic improvement in breeding for vitamin E content and improving the efficiency of breeding selection.

BRIEF DESCRIPTION OF THE DRA WINGS

In order to explain the embodiments of the present disclosure or the technical scheme in the prior art more clearly, the drawings needed in the embodiments will be briefly introduced below. Obviously, the drawings described below are only some embodiments of the present disclosure, and other drawings may be obtained according to these drawings without creative work for ordinary people in the field.

DETAILED DESCRIPTION OF THE EMBODIMENTS

Figure 1A:
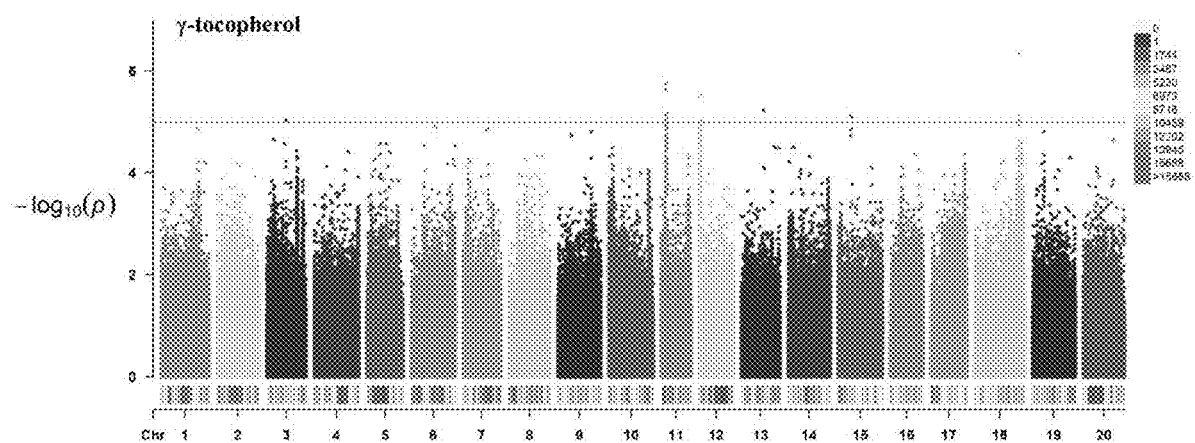
FIG. 1A is a Manhattan plot of the genome wide association study (GWAS) results for y-tocopherol, with the solid line represents the significant threshold-log (p-value) ≥5.
Figure 1B:
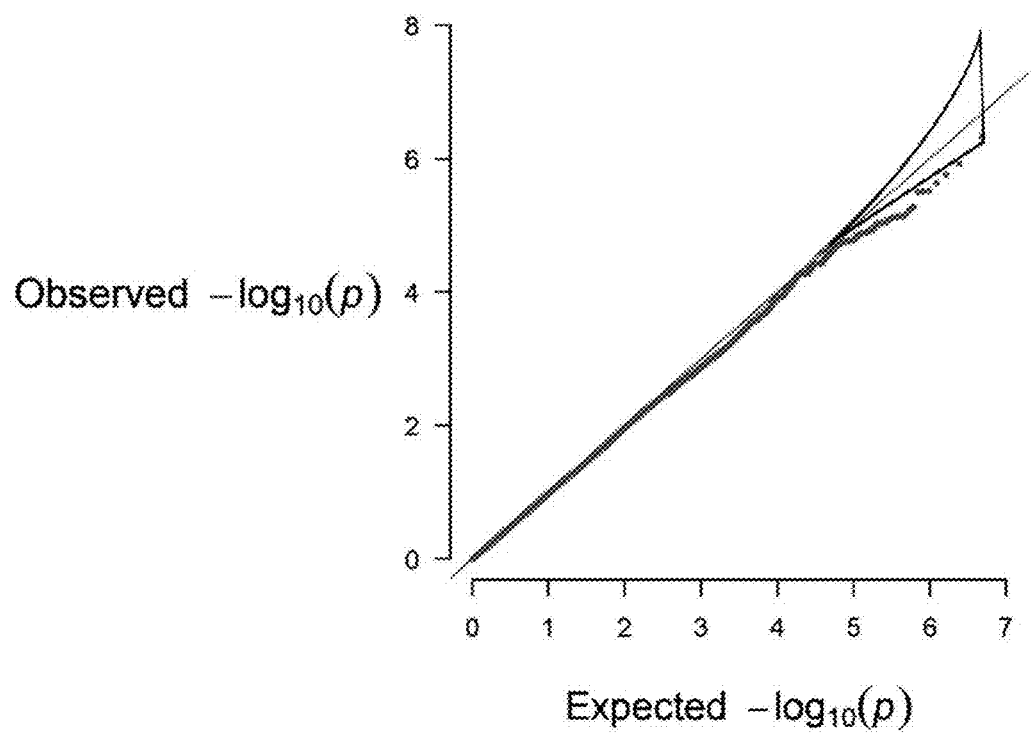
FIG. 1B is a Quantile-Quantile plot (QQ-plot) of the GWAS results for y-tocopherol.
Figure 1C:
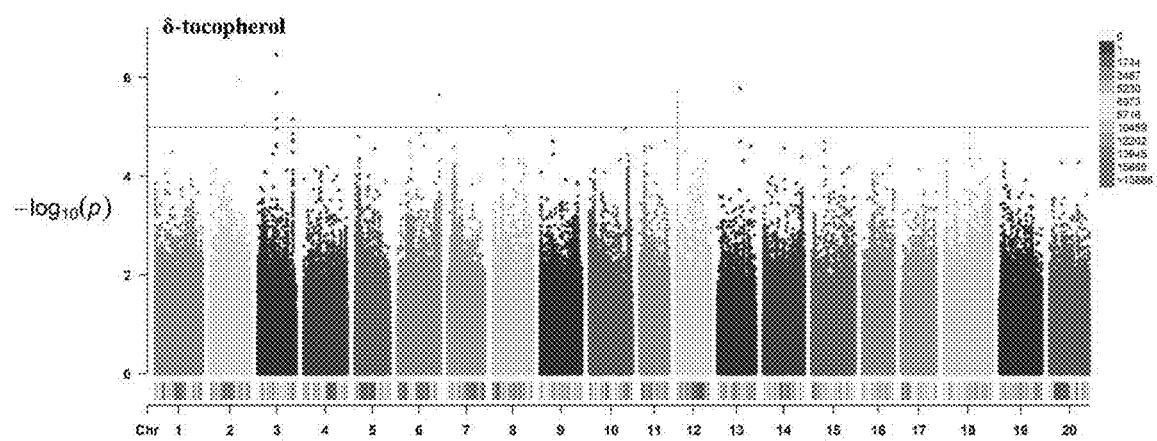
FIG. 1C is a Manhattan plot of the GWAS results for 8-tocopherol, with the solid line represents the significant threshold-log (p-value) ≥5.
Figure 1D:
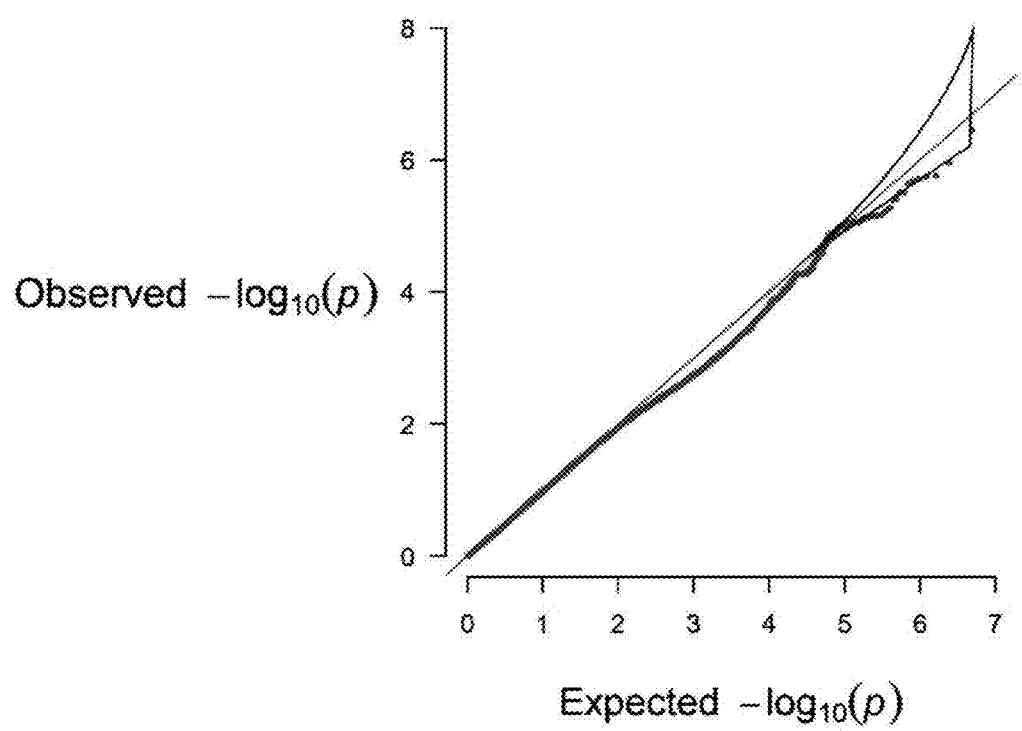
FIG. 1D is a QQ-plot of the GWAS results for 8-tocopherol.
Figure 1E:
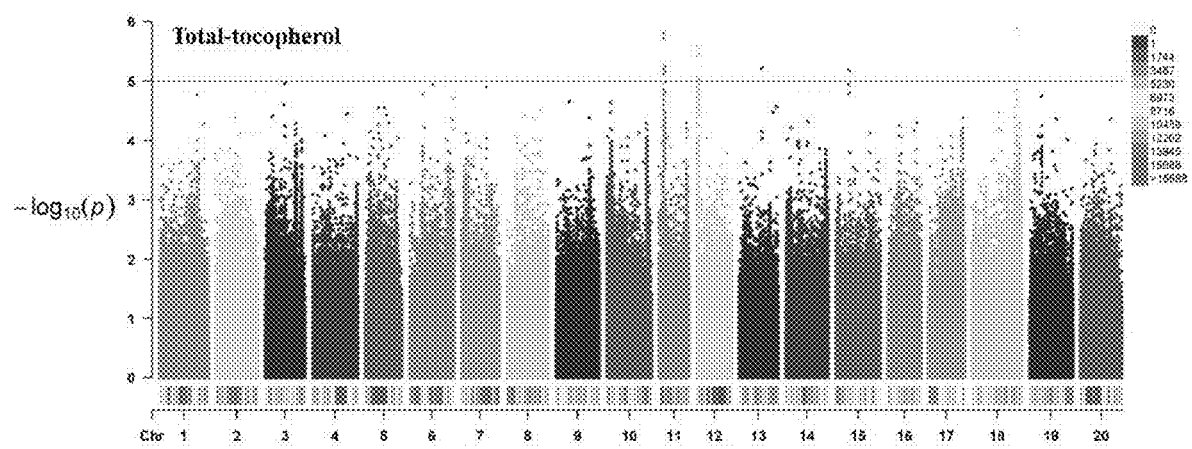
FIG. 1E is a Manhattan plot of the GWAS results for TVe, with the solid line represents the significant threshold-log (p-value) ≥5.
Figure 1F:
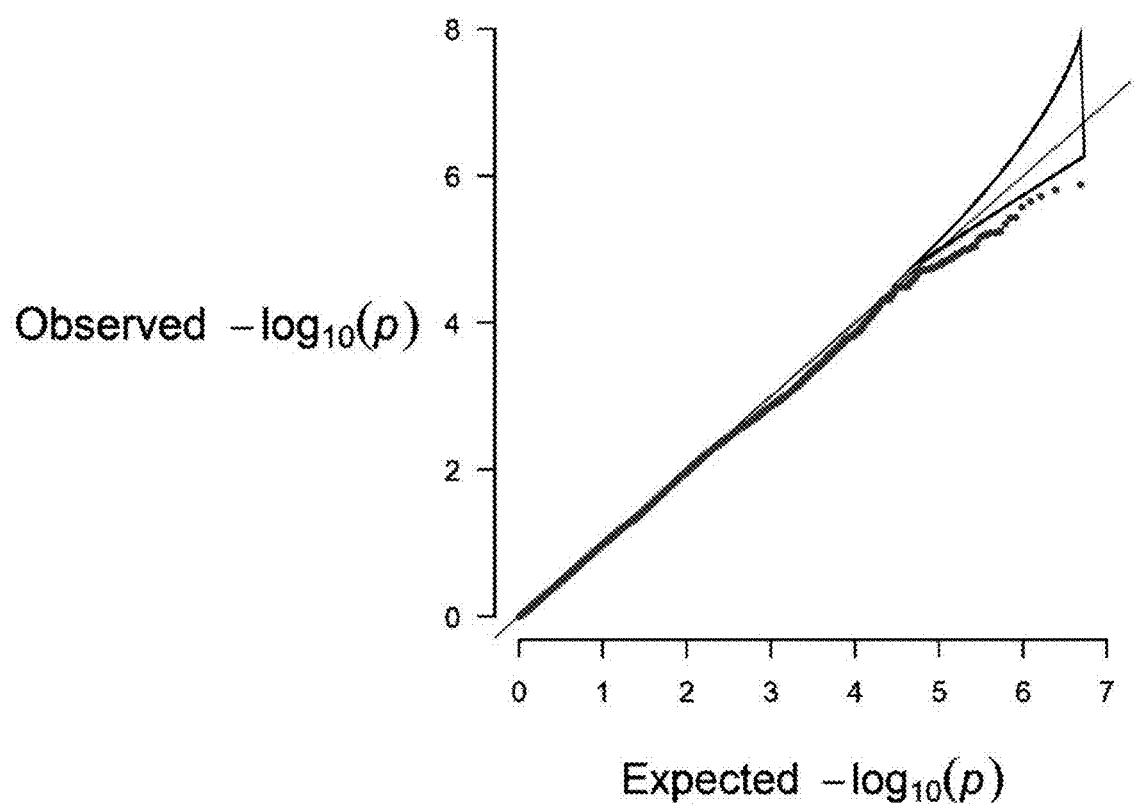
FIG. 1F is a QQ-plot of the GWAS results for TVe.

A number of exemplary embodiments of the present disclosure are now described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and embodiments of the present disclosure are exemplary only.

The terms "including", "comprising", "having" and "containing" used in this specification are all open terms, which means including but not limited to.

Embodiment 1 Obtaining Nucleotide Mutation Site (SNP) with Significant Correlation of Vitamin E Content in Soybean

1. DNA Extraction and High-Throughput Sequencing

From 1084 soybean germplasm resources, 264 representative soybean germplasm resources are selected (Table 1), including 52 landraces and 212 cultivars, which constitute the micro-core germplasm resources. Genomic DNA of 264 soybean leaves is extracted by CTAB method, and re-sequenced by 10× whole genome.

TABLE 1

Names and numbers of natural soybean populations used for resequencing and genome wide association study (GWAS)

| S/N | Names |
|---|---|
| NPS001 | NJ009 |
| NPS002 | Binhai green bean 036 |
| NPS003 | NJ015 |
| NPS004 | NJ022 |
| NPS011 | Liyang green bean 172 |
| NPS012 | Su 18-28 |
| NPS013 | Xuchi No.3 |
| NPS014 | Su 998 |
| NPS015 | 8301 |
| NPS016 | NX-661 |
| NPS017 | NX-F4-2 |
| NPS018 | NX-23-25 |
| NPS019 | NX-F5-1 |
| NPS020 | NX-NC-39 |
| NPS021 | NX-F7-13 |
| NPS022 | NX-F4-4 |
| NPS023 | NX-9484 |
| NPS024 | NX-F4-3 |
| NPS025 | NX-F5-8 |
| NPS026 | NX-NC-16 |
| NPS027 | NX-F5-5 |
| NPS028 | NX-F5-3 |
| NPS029 | NX-F7-59 |
| NPS030 | Gui 0513-2 |
| NPS031 | Gui 160 |
| NPS032 | Guichundou 113 |
| NPS033 | Huachun No. 6 |
| NPS034 | Ji 1507 |

TABLE 1-continued

Names and numbers of natural soybean populations used for resequencing and genome wide association study (GWAS)

| S/N | Names |
|---|---|
| NPS035 | Huachun No. 2 |
| NPS036 | Quandou 16 |
| NPS037 | Pudou No. 5 |
| NPS039 | Yuechun 20132 |
| NPS040 | 12B5 |
| NPS041 | Zhe 98002 |
| NPS042 | Xinghuadou No. 1 |
| NPS043 | Shoudou No. 3 |
| NPS044 | Liaoxiandou No. 12 |
| NPS045 | Xu bean 20 |
| NPS046 | Huai 9822 |
| NPS047 | Wandou 16 |
| NPS048 | Dongxin 2008-1 |
| NPS049 | Xu 8418 |
| NPS050 | Tongshan Swan Eggs |
| NPS051 | Wandou 30 |
| NPS052 | Qihuang 39 |
| NPS053 | Xudou No. 3 |
| NPS054 | Mix-selected large white carob |
| NPS055 | Xudou No. 2 |
| NPS056 | Zheng 9805 |
| NPS057 | Huaidou No. 5 |
| NPS058 | Huai 87-22 |
| NPS059 | Dongxin No. 3 |
| NPS060 | Zhonghuang 68 |
| NPS061 | Huaidou No. 3 |
| NPS062 | Huaidou No. 1 |
| NPS063 | Si 92-288 |
| NPS064 | Xudou No. 4 |
| NPS065 | Sidou 10-743 |
| NPS066 | Xudou No. 8 |
| NPS067 | Huaidou No. 9 |
| NPS068 | Guandou No. 3 |
| NPS069 | Wandou 20001 |
| NPS070 | Xing dou No. 3 |
| NPS071 | Zhoudou 23 |
| NPS072 | Hedou No. 2 |
| NPS073 | Wandou 21116 |
| NPS074 | Pudou 206 |
| NPS075 | Fendou 92 |
| NPS076 | Meng 119807-2 |
| NPS077 | Fendou 78 |
| NPS078 | Huaidou No. 4 |
| NPS079 | Xu 8212 |
| NPS080 | Xu 78107-6 |
| NPS081 | Xu 7027-19 |
| NPS082 | Huaidou 12 |
| NPS083 | Zheng 1440 |
| NPS084 | Jihuang 13 |
| NPS085 | Huai 91-07 |
| NPS086 | Xuzhou 126 |
| NPS087 | Xudou 135 |
| NPS088 | 8133-7 |
| NPS089 | Xudou No. 11 |
| NPS090 | Huaidou No. 6 |
| NPS09 | Xu bean 21 |
| NPS092 | Xu bean 18 |
| NPS093 | Ji NF58 |
| NPS094 | Fu 04-35 |
| NPS095 | Zheng 1539 |
| NPS096 | Huaidou 11 |
| NPS097 | Hedou 29 |
| NPS098 | Wandou 33 |
| NPS099 | Suike 8 |
| NPS100 | Siyang 209 |
| NPS102 | Qihuang28 |
| NPS103 | Huaidou 13 |
| NPS104 | Luodou 1 |
| NPS106 | Xudou 16 |
| NPS107 | Xu 8133-2 |
| NPS108 | Zhonghuang 24 |

TABLE 1-continued

Names and numbers of natural soybean populations used for resequencing and genome wide association study (GWAS)

| S/N | Names |
| --- | --- |
| NPS109 | Han 12-204 |
| NPS110 | Hedou 28 |
| NPS111 | Ganyun big four grains |
| NPS112 | Ji bean 17 |
| NPS113 | Huaidou No. 7 |
| NPS114 | Jindou 26 |
| NPS115 | Lu 99-10 |
| NPS116 | Zhonghuang 37 |
| NPS117 | Fendou 57 |
| NPS118 | Huai'an Wuzuidou A and B |
| NPS119 | Dafeng small green bean 038 |
| NPS120 | Zhoudou 19 |
| NPS121 | Xudou 135 |
| NPS122 | Fendou 6No. 1 |
| NPS123 | Meng 9418 |
| NPS124 | Si 91840 |
| NPS125 | Zhu 9715 |
| NPS126 | Ji B9 |
| NPS127 | Fudou No. 1 |
| NPS128 | Zhongdou 20 |
| NPS129 | Binhai Big White Flower |
| NPS130 | Shangdou No. 7 |
| NPS131 | Zhoudou No. 13 |
| NPS132 | Zhu 9712-1 |
| NPS133 | Shang 951099 |
| NPS134 | Zhoudou No. 5 |
| NPS135 | Yudou 27 |
| NPS136 | Xu 9210-2 |
| NPS137 | Kaidou No. 4 |
| NPS138 | Meng 9449 |
| NPS139 | He 93-1 |
| NPS140 | Doujiao 73 |
| NPS141 | Shanning No. 9 |
| NPS142 | Shanning No. 10 |
| NPS144 | Shangdou No. 1 |
| NPS145 | Meng 9235 |
| NPS146 | Meng 91413 |
| NPS147 | Fu 9605 |
| NPS148 | Zhonghuang 41 |
| NPS149 | Zhongyou 98C |
| NPS150 | Gaofeng No. 1 |
| NPS151 | Zhongyou 884-295 |
| NPS152 | Zhongyou 92-3214 |
| NPS153 | Yudou No. 2 |
| NPS154 | Lindou No. 10 |
| NPS155 | Xu 0701 |
| NPS156 | Peiyuan No. 1 |
| NPS157 | Jining 98-10645 |
| NPS158 | Jining 98-11497 |
| NPS160 | Huai 98-24 |
| NPS161 | Zhongdou No. 5 |
| NPS162 | Jidou 7 |
| NPS163 | Mengdou 8206 |
| NPS164 | Zheng 92029 |
| NPS165 | Wandou 24 |
| NPS166 | Zhu 944 |
| NPS167 | Zhou 9528-2 |
| NPS168 | Hedou No. 6 |
| NPS169 | Haoyu 56 |
| NPS170 | Jidou 1No. 2 |
| NPS171 | Zhongdou 20 |
| NPS172 | Zhoudou 12 |
| NPS174 | Wandou 28 |
| NPS175 | Wandou 905 |
| NPS176 | Zhonghuang 309 |
| NPS177 | Shi 1064 |
| NPS178 | Zheng 15283 |
| NPS179 | Zhongzuo 11-817 |
| NPS180 | Lu 0126 |
| NPS181 | Suike 45 |
| NPS182 | Wandou 0954 |
| NPS183 | Ji 16-J10 |
| NPS184 | Ji 16-J16 |
| NPS185 | Fandou No. 9 |
| NPS186 | Fandou 1510 |
| NPS187 | Nannong 1609 |
| NPS188 | Nannong 1608 |
| NPS189 | Shangdou H28 |
| NPS190 | Shi 1415 |
| NPS191 | Weidou 13 |
| NPS192 | Zhongdou 5701 |
| NPS193 | Zhou11019-2-1 |
| NPS194 | Luo4904 |
| NPS195 | Xu0366-9 |
| NPS196 | Zhudou 26 |
| NPS197 | Liudou 109 |
| NPS198 | Huadou No. 4 |
| NPS199 | Hi J14109 |
| NPS201 | Huachun No. 3 |
| NPS202 | Huachun No. 9 |
| NPS203 | Diandou No. 4 |
| NPS204 | Diandou 86-5 |
| NPS205 | Pudou 611 |
| NPS206 | Wandou 24 |
| NPS207 | Wandou 37 |
| NPS208 | Wandou 38 |
| NPS209 | Zhonghuang 302 |
| NPS210 | Zhonghuang 306 |
| NPS211 | Guichun No. 1 |
| NPS212 | Guichun No. 11 |
| NPS213 | Guichun No. 12 |
| NPS214 | Guichun 16 |
| NPS215 | Guichundou 107 |
| NPS216 | Guichundou 111 |
| NPS217 | Guichundou 112 |
| NPS219 | Gui 0508-3 |
| NPS223 | Gui 1603 |
| NPS224 | Gui 26BC2-7 |
| NPS225 | Qiandou No. 6 |
| NPS226 | Qiandou No. 8 |
| NPS227 | Zhongdou 33 |
| NPS228 | Zhongdou 41 |
| NPS229 | Xiangchundou 24 |
| NPS230 | Quandou No. 4 |
| NPS231 | Quandou 17 |
| NPS232 | East China Sea big soybean 132 |
| NPS233 | Sudou 13 |
| NPS234 | Taixingjiu 110 |
| NPS235 | Nannong 15-3 |
| NPS236 | Nantong 072 |
| NPS237 | Pudong Flat 130 |
| NPS238 | 12144 |
| NPS239 | Xiangyu No. 1 |
| NPS240 | 12078 |
| NPS241 | Suxian 16-12 |
| NPS242 | Tongdou No. 6 |
| NPS243 | Danyang late season bean 161 |
| NPS244 | 8416 Taizhou Baihuawu B |
| NPS245 | Suxia 5006 |
| NPS246 | Shuyang small 020 |
| NPS247 | Pudongguan green bean |
| NPS248 | Haimenyang 104 |
| NPS249 | Nannong S5-1 |
| NPS250 | Su 16-12 |
| NPS251 | 12108 |

TABLE 1-continued

Names and numbers of natural soybean populations used for resequencing and genome wide association study (GWAS)

| S/N | Names |
| --- | --- |
| NPS252 | Nantong 071 |
| NPS253 | YIxingwan 120 |
| NPS254 | Nantong small yellow shell 070 |
| NPS255 | Qidong dill bean 062 |
| NPS256 | 12120 |
| NPS258 | East China Sea peach 005 |
| NPS259 | Tongdou 07-195 |
| NPS260 | Dongtai A 044 |
| NPS261 | C019 |
| NPS263 | Qidong Green Ox 065 |
| NPS264 | C019 |
| NPS265 | C18 |
| NPS266 | Yancheng 041 |
| NPS267 | nameless |
| NPS268 | nameless |
| NPS269 | Happy Green |
| NPS270 | Qihuang 34-2 |
| NPS271 | L2015D-4 |
| NPS272 | Su 14-2 |
| NPS273 | Binhai black bean 100 |
| NPS274 | Nannong 415 |
| NPS294 | August white |
| NPS295 | Binhaiju 033 |
| NPS296 | Xinyi Great Purple Flower |
| NPS297 | Pixian Langxing 147 |
| NPS298 | Haimen green bean 057 |
| NPS299 | Sudou 18 |
| NPS300 | Sudou 16 |
| NPS301 | Qihuang 35 |
| NPS302 | Lu 93060 |

Note: all of the above 264 soybean materials in the form of the corresponding numbers in Table 1 appear in the published literature (Zhang, W., Xu, W., Zhang, H. et al. *Comparative selective signature analysis and high-resolution GWAS reveal a new candidate gene controlling seed weight in soybean. Theor Appl Genet* (2021). https://doi.org/10.1007/s00122-021-03774-6).

2. Determination of Vitamin E Content

From each family line, 10.00 to 15.00 g of soybean seeds of full grain and uniform size are selected and crushed by sample milling (FOSS, Knifetec1095) for 60 sec; 0.2 g of crushed soybean powder sample is weighed, and added with 0.05 g of vitamin C (Vc) and 4 mL of 80% ethanol solution to mix, and then ultrasonicated for 30 min at low temperature in a water bath; then, 8 mL of n-hexane solution is added; finally, after ultrasonication at low temperature water bath for 30 min and centrifugation, the supernatant is taken and passed through 0.22 μm organic phase filtration membrane. Using high performance liquid chromatography (HPLC) and external standard method, the isomers of vitamin E tocopherol are quantitatively analyzed. The chromatographic column is a product of DIKMA Company, and the packing of chromatographic column is symmetry, with diamond C18, 5 μm, and the column size is 250.0 mm×4.6 mm; the excitation wavelength of fluorescence detector is 290 nm and the emission wavelength is 300 nm. The mobile phase is methanol with a flow rate of 1.0 mL/min, and column temperature 35° C., the sampling volume is 20 μL, and the detection duration is 10 min. The peak areas of γ-tocopherol and δ-tocopherol are substituted into the regression equation for quantitative analysis. TVe is the sum of α-tocopherol, γ-tocopherol and δ-tocopherol values.

3. Genome-Wide Association Study (GWAS)

Using GAPIT algorithm package in R language software, the calculation model is mixed linear model (MLM) for genome-wide association study (GWAS). After elimination and filtering, 199 SNP loci significantly associated with vitamin E content in soybeans are detected (FIG. 1A-FIG. 1F), among them, the SNP locus S12_980498, which is significantly associated with soybean vitamin E with 9.6% explained phenotypic variance, is located at chromosome 12, position 980,498 bp in soybean genome v2.0.

The gene sequence containing the SNP locus is shown in SEQ ID NO. 1:

AAACTTTATATTATTTTATT[A/T]ATGTTATTCACTATTCATCCAGCA

ATGTAATGTACATGGTAAAAAATTGTTCAGTAACTCAATTATGTTTGTG

GTGTGTTATTTTTTTTGTTGTCATATATTTTAGTGTGTATGAAATGGAC

CCTTAAAAGAATAATGACGAGATCCTAAACTAACACCATTTCATATTCA

TACTAATGAAAAGAAGGAGAAGAGGAAACACGTGGTGTCATAGTTTGGG

TCAATTTGGAATGGGCTGAAATGACAGGGCCAGAAGGAATTGGGCCCTT

GGAGAAGTAGGCTTGGGGCCCATTGGTTGGAGGAACAAATAAAGGAAGG

GAAGGGAAGAGTGAAAGCGAGACGTTAGCTGGGCAAAGCAACCGGACAC

ACCCCAACCTGACTT (Note: the 21 bp of the sequence shown in SEQ ID NO. 1 is an SNP locus, and there is A/T mutation at this locus).

Embodiment 2 Development of Specific Primers for KASP Marker

Using the Primer-BLAST function of NCBI (https://www.ncbi.nlm.nih.gov/), three primers are designed according to the sequence of SEQ ID NO. 1, namely, the upstream primer F1 (SEQ ID NO. 2), the upstream primer F2 (SEQ ID NO. 3) and the downstream primer R (SEQ ID NO. 4), where F1 and F2 respectively include the FAM and HEX fluorescent junction sequences (underlined), the sequences of which are shown below:

forward primer F1 (SEQ ID NO. 2):

5'-GAAGGTGACCAAGTTCATGCTAAACTTTATATTATTTTATTT-3';

forward primer F2 (SEQ ID NO. 3):

5'-GAAGGTCGGAGTCAACGGATTAAACTTTATATTATTTTATTA-3';

reverse primer R (SEQ ID NO. 4):

5'-AAGTCAGGTTGGGGTGTGTC-3'.

Embodiment 3 Detection of Genotypes of SNP Loci in Different Soybean Varieties and its Application Twenty-eight soybean materials are randomly selected, and the genomic DNA of soybean samples is extracted respectively. Using the genomic DNA as a template, the PCR amplification products are obtained by using the special primers developed in Embodiment 2. PCR amplification is carried out in ABI7500 real-time fluorescence quantitative PCR instrument. After PCR, the instrument performs genotyping according to fluorescence signals. The amplification systems are all 10 μL reaction systems: 25 ng/μL soybean sample DNA template 2 μL, 2×KASP Master mix 5 μL, KASP mixed primer 0.14 μL, where F1:F2:R=2:2:5 (V/V/V), and water 2.86 μL. The reaction conditions include activation at 94° C. for 15 min, denaturing at 94° C. for 20 sec, annealing at 61-55° C. for 60 sec, decreasing 0.6° C. per cycle for 10 cycles; denaturing at 94° C. for 20 sec, annealing at 55° C. for 60 sec for 26 cycles.

Figure 2:
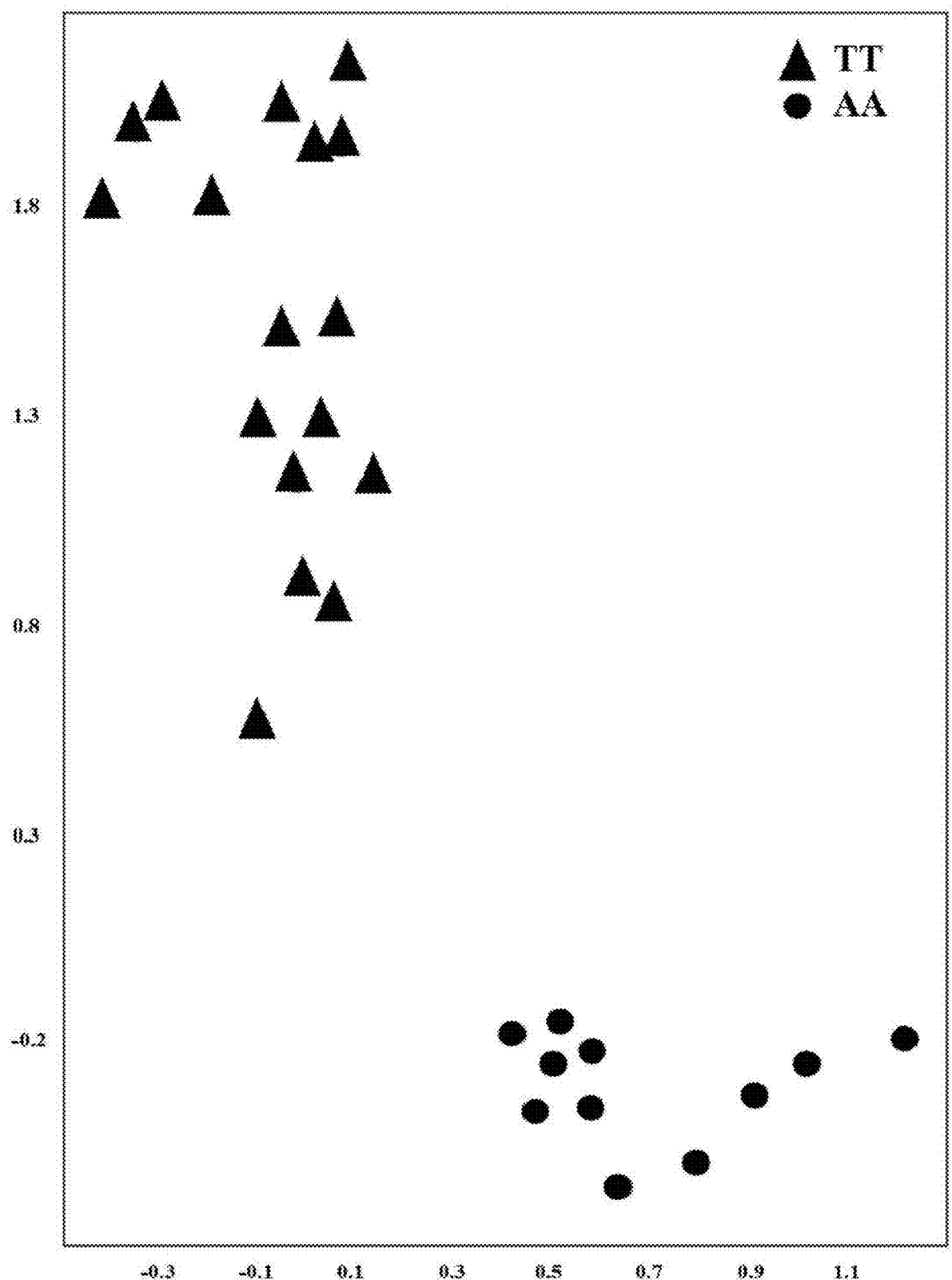
FIG. 2 shows the genotyping results of different soybean varieties with special primers for KASP markers. The triangles near the Y axis and the black dots near the X axis represent soybean varieties with T allele and soybean varieties with A allele, respectively.

After the reaction is completed, ABI7500 real-time fluorescence quantitative PCR instrument directly reads the fluorescence data of PCR reaction products, and the result is shown in FIG. 2.

The triangles near the Y-axis are the loci carrying the T allele variant with genotype TT, and there are 17 soybean varieties with average γ-tocopherol, δ-tocopherol, and TVe contents of 215.37 micrograms per gram (μg/g), 24.36 μg/g, and 256.43 μg/g, respectively; When the amplification reaction is carried out, the detection sample will combine with the specific FAM detection primer and release the blue fluorescent groups. With the increase of the number of PCR reaction cycles, the blue fluorescent signal is enhanced.

The black dots near the X-axis are the loci carrying the A allelic variant with genotype AA, and there are 11 copies with average γ-tocopherol, δ-tocopherol, and TVe contents of 160.35 μg/g, 17.69 μg/g, and 190.25 μg/g, respectively; when the amplification reaction is carried out, the detection sample will combine with the specific HEX detection primer and release the red fluorescent groups. With the increase of the number of PCR reaction cycles, the red fluorescent signal will be enhanced.

According to Embodiment 1, it is found that in the association analysis population containing 264 soybean materials (13 materials are genotyped as deletion at SNPS12_980498), the average contents of γ-tocopherol, δ-tocopherol and TVe of 129 soybean materials with AA genotype are 160.88 μg/g, 19.24 μg/g and 192.69 μg/g, respectively. The average contents of γ-tocopherol, δ-tocopherol and TVe in 122 soybean materials with TT genotype are 214.52 μg/g, 25.35 μg/g and 256.65 μg/g, respectively.

Accordingly, when soybeans are measured using the KASP marker-specific primers developed in Embodiment 2, if a blue fluorescent signal appears in the result, the soybean is determined to be a genotype with a high content of vitamin E. If a red fluorescent signal appears in the result, the soybean is determined to be a genotype with a low vitamin E content. The detection results are consistent with those of Embodiment 1.

The above-mentioned embodiments only describe the preferred mode of the present disclosure, and do not limit the scope of the present disclosure. Under the premise of not departing from the design spirit of the present disclosure, various modifications and changes made by ordinary technicians in the field to the technical scheme of the present disclosure shall fall within the protection scope determined by the claims of the present disclosure.

What is claimed is:

1. A KASP primer set for detecting a molecular marker significantly associated with vitamin E content in soybeans, comprising an upstream primer F1 that comprises SEQ ID NO: 2, an upstream primer F2 that comprises SEQ ID NO: 3, and a downstream primer R that comprise SEQ ID NO: 4.

2. A method for genotyping a molecular maker at nucleotide 21 of SEQ ID NO: 1 comprising:

performing fluorescence quantitative PCR amplification on a PCR amplification mixture that comprises genomic DNA from a soybean sample and the KASP primer set of claim 1, reading a fluorescence signal after PCR amplification, analyzing and converting the fluorescence signal, and identifying a genotype, wherein, if the genotype is identified as TT, the soybean sample is determined to have a high vitamin E content, and if the genotype is identified as AA the soybean sample to be detected is determined to have low vitamin E content.

3. The method according to claim 2 wherein the fluorescence quantitative PCR amplification comprises heating the PCR amplification mixture to 94° C. for 15 minutes;

carrying out 10 cycles of denaturation at 94° C. for 20 seconds and annealing for 60 seconds, where in the first annealing cycle the annealing temperature is 61° C. and the temperature is decreased by 0.6° C. per cycle for each of the next nine cycles; and carrying out 26 cycles of denaturation at 94 C for 20 seconds and annealing at 55° C.

4. The method according to claim 2, wherein the fluorescence quantitative PCR amplification mixture comprises:

2 μL of 25 ng/μL genomic DNA template from soybean, 0.14 μl of the KASP primer set, wherein a volume ratio of the upstream primer F1, upstream primer f2 and downstream primer R is 2:2:5, and 2.86 μl water.

* * * * *

```
                          SEQUENCE LISTING

Sequence total quantity: 4
SEQ ID NO: 1            moltype = DNA  length = 403
FEATURE                 Location/Qualifiers
source                  1..403
                        mol_type = other DNA
                        organism = synthetic construct
SEQUENCE: 1
aaactttata ttattttatt watgttattc actattcatc cagcaatgta atgtacatgg    60
taaaaaattg ttcagtaact caattatgtt tgtggtgtgt tatttttttt gttgtcatat   120
attttagtgt gtatgaaatg gacccttaaa agaataatga cgagatccta aactaacacc   180
atttcatatt catactaatg aaaagaagga gaagaggaaa cacgtggtgt catagtttgg   240
gtcaatttgg aatgggctga aatgacaggg ccagaaggaa ttgggcccct ggagaagtag   300
gcttggggcc cattggttgg aggaacaaat aaaggaaggg aagggaagag tgaaagcgag   360
acgttagctg ggcaaagcaa ccggacacac cccaacctga ctt                     403

SEQ ID NO: 2            moltype = DNA  length = 42
FEATURE                 Location/Qualifiers
source                  1..42
                        mol_type = other DNA
                        organism = synthetic construct
SEQUENCE: 2
gaaggtgacc aagttcatgc taaactttat attattttat tt                       42

SEQ ID NO: 3            moltype = DNA  length = 42
FEATURE                 Location/Qualifiers
source                  1..42
                        mol_type = other DNA
                        organism = synthetic construct
SEQUENCE: 3
gaaggtcgga gtcaacggat taaactttat attattttat ta                       42

SEQ ID NO: 4            moltype = DNA  length = 20
FEATURE                 Location/Qualifiers
source                  1..20
                        mol_type = other DNA
                        organism = synthetic construct
SEQUENCE: 4
aagtcaggtt ggggtgtgtc                                                20
```